United States Patent [19]

Gouet et al.

[11] Patent Number: 4,602,955

[45] Date of Patent: Jul. 29, 1986

[54] COMPOSITE MATERIAL THAT CAN BE USED TO MAKE OXYGEN SENSORS

[75] Inventors: Michel Gouet; Dominique Especel, both of Paris; Marianne Goge, Creteil, all of France

[73] Assignee: Electricite de France, Paris, France

[21] Appl. No.: 682,167

[22] Filed: Dec. 31, 1984

[30] Foreign Application Priority Data

Dec. 16, 1983 [FR] France .................. 83 20322

[51] Int. Cl.$^4$ .............................. C22C 29/12
[52] U.S. Cl. ...................... 75/234; 73/27 R; 75/235; 264/60; 264/332; 338/34; 419/19; 419/20; 428/552; 428/564; 428/633; 428/651; 428/660
[58] Field of Search .............. 419/2, 5, 7, 8, 9, 19, 419/20; 73/27; 338/34; 264/60, 332; 75/234, 235; 428/552, 564, 633, 651, 660

[56] References Cited

U.S. PATENT DOCUMENTS

| | | | |
|---|---|---|---|
| 4,102,678 | 7/1978 | Gothard et al. | 419/9 |
| 4,224,085 | 9/1980 | Brendel et al. | 419/8 |
| 4,256,810 | 3/1981 | Doubrava | 419/2 |
| 4,507,262 | 3/1985 | Karas et al. | 419/2 |

Primary Examiner—Stephen J. Lechert, Jr.
Attorney, Agent, or Firm—Robert E. Burns; Emmanuel J. Lobato; Bruce L. Adams

[57] ABSTRACT

A composite material sensitive to weak variations of oxygen pressure at a low temperature, of the type containing microscopic particles of an ionic conductor of oxygen ions contained in a solid solution, in tetravalent metal oxides, oxides of other metals with a valence less than four, other than the said of such a solid solution, the material contains discrete microscopic particles of an electronic conductor.

10 Claims, 11 Drawing Figures

COMPOSITE MATERIAL THAT CAN BE USED TO MAKE OXYGEN SENSORS

BACKGROUND OF THE INVENTION

The solidification in solution of oxides metals which have a lower oxidation degree (Ca, Mg, rare earths such as Y, Sc, Sm, Pr) than those of certain tetravalent metal oxides (Zr, Ce, Th, Hf), is accompanied by the formation of anionic lacunas, which confer to the solid solution an ionic conductivity extremely selective to oxygen, and therefore this material may be considered as a real solid electrolyte.

Therefore, if the two faces of such a material are exposed to different oxygen pressures, a difference of potential appears. Conversely, the application of an electric current to this material by two external electrodes provokes an actual "pumping" of oxygen through the solid, the flow of which is proportional to the intensity of the current applied.

This property has already been used for oxygen dosing; these devices are called potentiometric sensors, where the response, between 700° and 900° C., is ideal: its precision is 1% between 1 to $10^{-8}$ atm. They are mostly used to control and to regulate the air-petrol mixture in internal combustion engines and in metallurgical ndustries.

However, this relatively low operating temperature range still limits the applications of these materials. Effectively, whereas a lower utilization temperature could be desirable for many uses, it was noted that a temperature decrease results first of all in greater resistance of the material at low temperature and secondly, in a slowing down of the kinetics of the oxido-reduction reactions on the electrode. The result is that below 600° C., the response times of these devices become excessive which causes errors that may be imputed to complex and badly controlled phenomenons between the opposing phases of the electrodes.

Some researchers have tried to compensate for these inconveniences by selecting the materials and by improving the morphology of the electrodes, but they have not yet obtained results that can be used industrially. However, it can be admitted that, during the complex and unknown processes of transferring loads to interfaces between the three opposing phases of the electrodes ("electrolyte" solid solution, metallic electrode and gaseous oxygen), the kinetics of the electrochemical reaction, and as a result the electric current going through the interface, are limited by the slower process, which is linked to the oxygen pressure. In other words, the electrodes-electrolyte-gas interfaces present a resistance to the electric current going through, designated by "electrode resistance", which depends on the oxygen pressure, according to a relation which is a function of numerous parameters, but which, for a given electrodes-electrolyte combination and a given microstructure, is well defined and reproducible.

SUMMARY OF THE INVENTION

The present invention aims for a new composite metal-electrolyte type solid material, wherein the above-discussed relation is particularly favorable for applications which up to now were not possible for this kind of material.

To this effect, the invention involves a material of the kind mentioned before, but which has two phases, one which presents an ionic conductivity, and the other an electronic conductivity. In other words, the invention focuses on a new composite material, consisting on one hand of known particles of a solid electrolyte consisting of a solid solution of bivalent or trivalent oxides in tetravalent metal oxides, and on the other hand, particles of metal, all of these particles being dispersed in an aleatory manner in an noncontiguous or discrete state, by firing or fritting, either alone or with a nonconductive carrier material.

In particular in combination with, the solid electrolyte considered to be known, for example a yttriafied zircon, the metal, by preference will be a metal, such as platinum, gold, palladium or silver, in a proportion up to about 80% by weight and about 40 to 50% in weight.

It must be noted that in U.S. Pat. No. 4,138,881, an apparently similar system is described in which the same phenomenon is used:

An electric current cannot go through a metal/oxide or oxide/metal interface, unless there is an electrochemical reaction of this type:

Such a reaction requires the presence of a metal (which attracts or repels electrons), of the oxide (which attracts or repels the oxygen ions), but also of oxygen, that is, more or less in sense (1). It has been noted that the speed of this reaction, and therefore the overall electric current, is function of the partial pressure of this oxygen.

This phenomenon is noted in the U.S. patent mentioned above in order to determine the passage of an electric current at a high temperature between a solid electrolyte layer and a porous layer of cerium metal in the presence of oxygen in the surrounding atmosphere. If a continuous tension is applied between the two ends of such a structure, and if the current must pass through metal/oxide interfaces in order to go through the structure, the intensity of the current will be limited by the kinetics of the interface, and therefore will depend on the partial pressure of the oxygen: the system may therefore be used to measure variations of this pressure, which is also the aim of the present invention.

However, the technique used in the system of the above-mentioned U.S. patent is distinguished itself from the one in this present invention by the following points:

1. The cerium metal used in the system of the above-mentioned U.S. patent requires a metal content sufficient for continuous metallic (electronic) conduction: the cerium metal layer conductivity is therefore of a metallic nature, i.e. the metal must have "percolated" the cerium metal material.

However, in the present invention, the metal contained in the cerium metal is formed of noncontiguous or discrete microparticles, and therefore cannot constitute a continuous path for the electric current. This current must be successively electronic then ionic to go from one particle to the other, and it is precisely the flow of the current from the ionic form to the electronic form and inversely, which is used in the present invention, which uses a cerium metal nonpercolated by the metal.

2. The system of the above-mentioned U.S. patent requires an ionic conductor support (solid electrolyte), in addition to the cerium metal. On the contrary, in the present invention, it is pointless to use a solid electrolyte in addition to the one that is included in the composition of the cerium metal, even thought a support to the cerium metal can be provided, and this support can then be of the same nature as the electrolyte contained by the cerium metal: anyway, this support plays no part in the operation of the sensor.

It is important to note that it is the microstructure of the cerium metal that is sensitive in itself, even without support, for this structure imposes a multiplication of metal/oxide interface crossings by the current, the resistance of these interfaces being the parameter which depends on the oxygen pressure on which the operation of the system is based, according to the invention.

In order to realize this microstructure, the size of the particles remains in the usual intervals for microscopic particles, it being understood that the increase in metal-electrolyte interfaces, each one playing the role of an electrochemical cell, leads to a pseudo-ionic oxygen conduction, which depends on the oxygen pressure. The present invention for the production of oxygen sensors is based on this phenomenon: while the electric conductivity of each of the individual constituents is insensitive to the oxygen pressure, the necessity of electrochemical reactions depending on the oxygen potential at the level of each interface to ensure the transfer of the current, makes the conductivity of all of them depend on the presence of oxygen. The variable that is used is the apparent resistance of the constituted assembly of a large number of such cells.

BRIEF DESCRIPTION OF THE DRAWINGS

Other features and characteristics of the composite material are illustrated in the appended claims and drawing in which:

DESCRIPTION OF THE PREFERRED EMBODIMENTS

For example, in the following, the composition and the performance of several devices produced according to the invention will be related.

EXAMPLE 1

Figure 1:
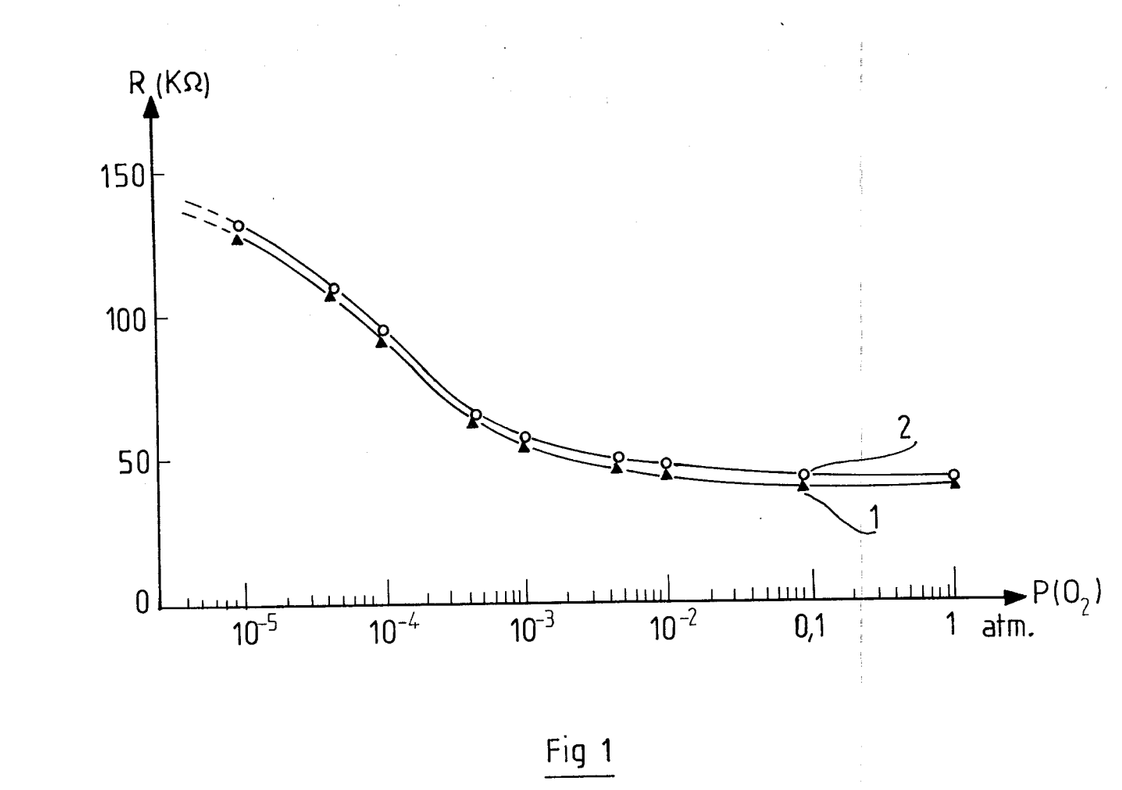
FIG. 1 is a diagram of a curve illustrating resistance variations to direct current of the composite material, according to the invention, at different oxygen pressures.

The device is prepared by firing at 1200° C. two electrodes made of platinum wires of 0.5 mm diameter, separated by a 5×5 mm layer of material, formed by a dispersion of a 30% mass of yttriafied zircon (8% molar) and of a 70% mass of platinum powder, in an organic carrier of the kind usually used for serigraphics, which disappears during firing. After firing, a mixed platinum zircon is obtained, of a porosity of about 40% in volume, separating the two platinum electrodes. P This device is introduced into a controlled atmosphere furnace ($O_2+Ar$), heated to 800° C., and its apparent resistance to a direct current of potential differences of 2.5 v (Curve 1), 10 v (Curve 2) . . . was noted. The results of these measurements appear in the curves in FIG. 1. These curves indicate that if this resistance varies very slightly under high oxygen pressures, on the contrary, below 1% the resistance increases rapidly, until it can be multiplied by 2.5 to $10^{-4}$ atm.

EXAMPLE 2

A second device is produced by the deposit of two platinum lacquer electrodes on a substratum of alumina, 2 cm long and 2 mm apart, connected to nickel-chromium alloy electrodes. A paste of the composite platinum material (50% by mass)-yttriafied zircon material (50% by mass) is applied between the two electrodes, and the whole is fired to 1400° C. for 6 hours.

Figure 2:
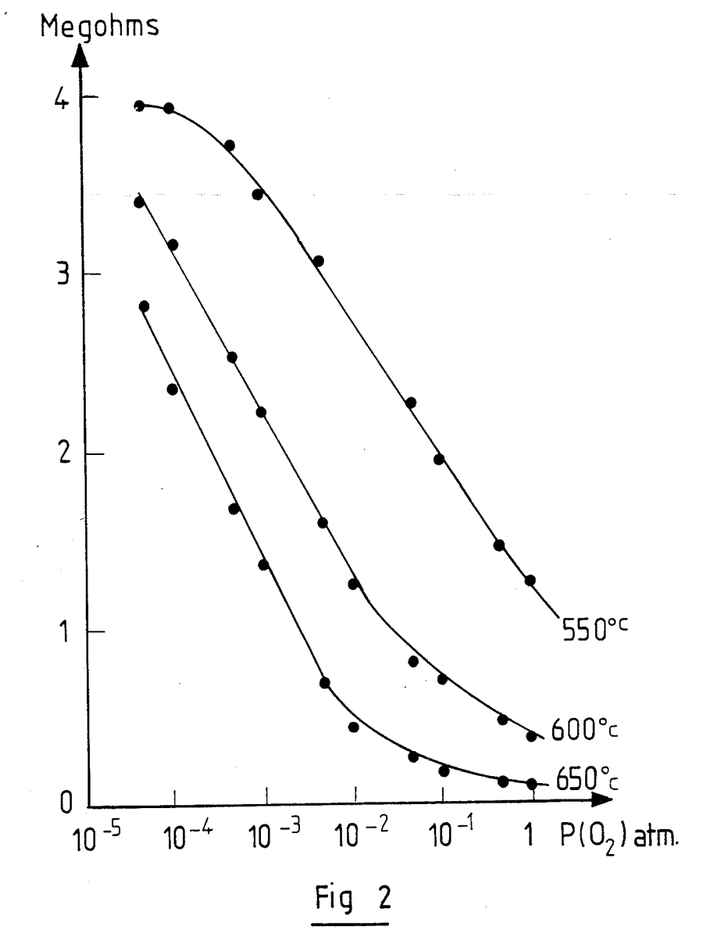
FIG. 2 is a diagram of a curve of apparent resistance to a direct current under changing oxygen pressures.

The device is then introduced into a controlled atmosphere furnace, as above, and its apparent resistance is noted, measured in direct current (0.1 micro ampere) at 550, 600 and 650° C. The results shown in FIG. 2 indicate that, for example at 550° C., resistance increases regularly when oxygen pressure decreases, increasing notably by a factor 3 between 1 to $10^{-3}$ atm.

Several oxygen pressure flushings and new measurements after cooling and reheating the device confirmed the reproducibility of this performance.

EXAMPLE 3

To show results that can be obtained between 350° and 500° C. with layers applied by a brush, the following process was used:

A. Cerium metal composition:
  Yttriafied zircon powder (88% $ZrO_2$, 12% $YzO_2$ by mass), passed through a 400 Mesh sieve
  Platinum paste for serigraphy: Demetron origin.

The platinum is in the form of flakes that are a maximum of 12 microns in length, the composition of the organic carrier (which disappears during firing) is unknown. The exact platinum content is determined by calcination. It is 75% by weight.

Mixtures are obtained by weighing, with proportions of zircon powder and platinum paste which allow obtaining after calcination and fritting platinum proportions from 40.50 to 60% (by weight).

B. Preparation of samples:

Alumina rods containing eight circular canals and coated with successive layers of platinum and cerium metal are circularly cut so that each one has five samples. Two canals are used as a thermocouples which constitutes a common electrode, the six others guide the nickel-chromium wires, which constitute a common electrode, and the second electrode of each of the five samples.

Figure 3:
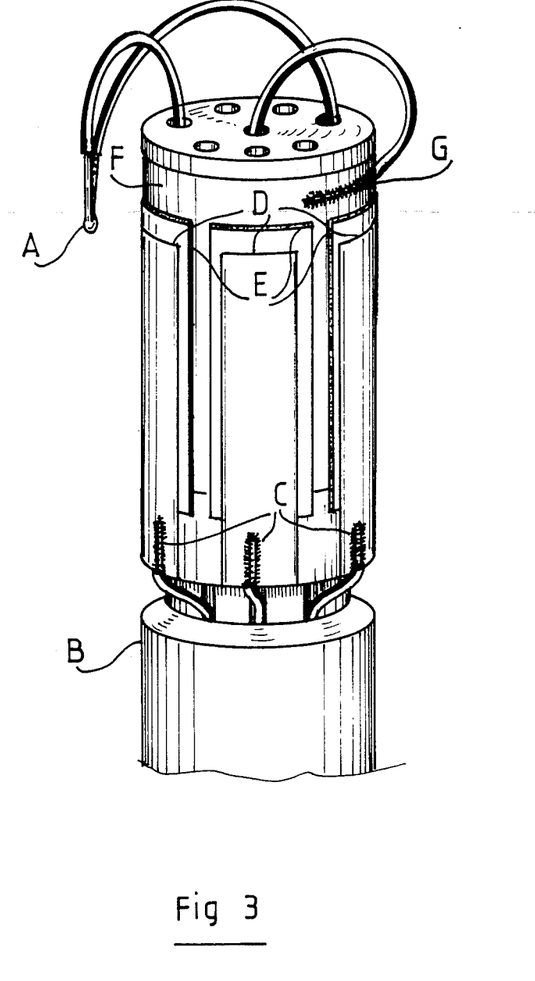
FIG. 3 is a schematic diagram of testing of samples according to the invention.

This device is schematically illustrated in FIG. 3, in which the following components are illustrated:

A Chromel-alumel thermocouple
B Alumina support rod with eight canals
C Electrodes welded together by a drop of platinum lacquer
D External platinum lacquer layer
E Cerium layers to be measured
F Platinum lacquer layer common to the five samples
G Common electrode welded by a drop of platinum lacquer.

The surfaces of metallic electrodes understudied are rectangles of about 2.5 mm × 8 mm.

The thickness of the obtained layers is about 10 microns after firing. (Evaluated by weighing with a supposed porosity of 30%).

The first tests having only one layer of cerium metal resulted in a short circuit between the metallic electrode ends.

Other tests were made with seven successive deposits of cerium metal (0.08 mm average total thickness). The deposit procedure is the following:

Deposit by brush of a platinum paste electrode, fritting at 1450 degrees for 2 hours.

Three double deposits of cerium metal paste, with a drying in a furnace at 200 degrees for 1 hour after each deposit, and fritting at 1450 degrees for 2 hours every two deposits.

Deposit of one layer of cerium metal, followed by a drying, then a deposit of an external platinum paste electrode, and finally drying, and fritting at 1450 degrees for 5 hours.

In these conditions the samples are not short circuited, except for those which contain 60% of platinum (two out of five) and the adherance of the different layers is perfect.

Nickel-chromium alloy wire electrodes (5/10 mm diameter) are then introduced into the canals of the alumina rods, placed in contact with the extreme platinum layers, and glued by a drop of platinum paste. The device is then introduced into the measuring furance, raised to 1000 degrees in the air for 12 hours, sealing the electrodes, and then studied from the electric view point.

C. Influence of the oxygen pressure on the apparent resistance:

Measuring is done in a temperature regulated furnace in an atmosphere of a mixture of nitrogen and oxygen of variable compositions.

Figure 4:
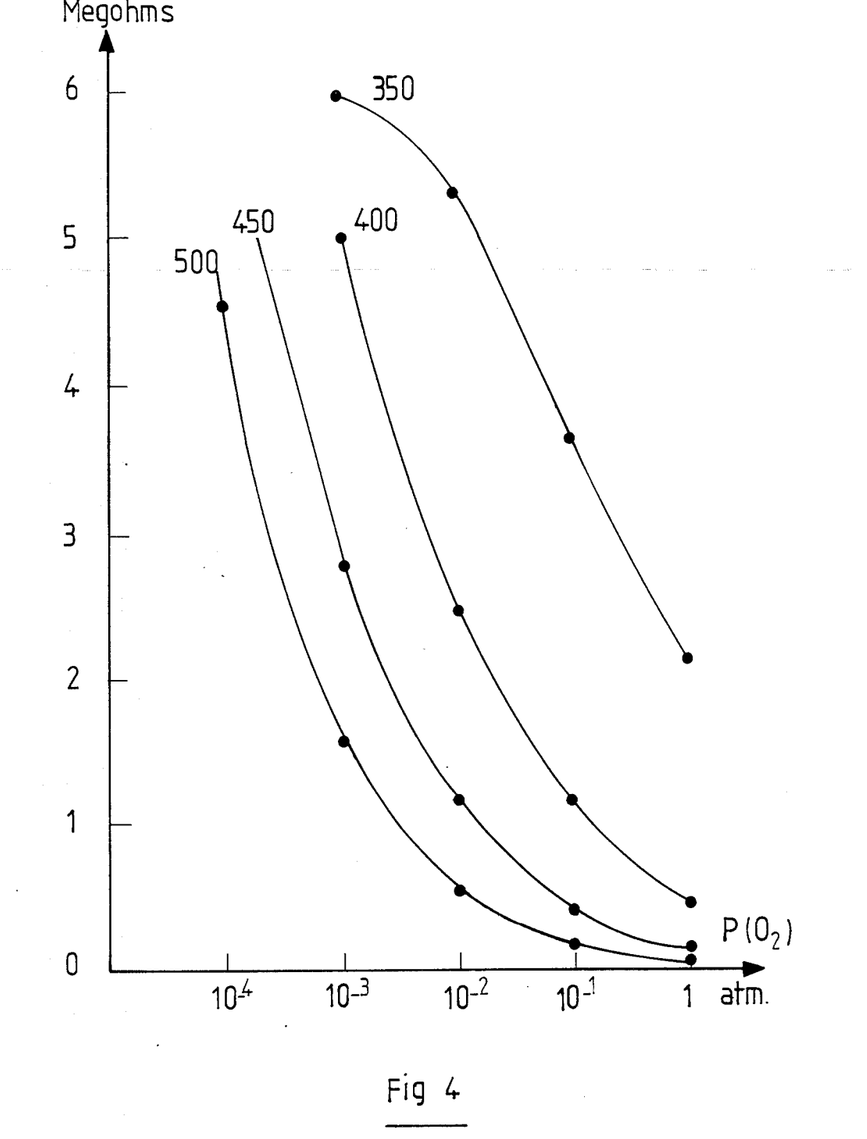
FIG. 4 is a diagram of curves of apparent resistance of a sample according to the invention.

The curves in FIG. 4 show the typical evolution of the apparent resistance, for a sample containing 40% by weight of platinum. All of the other samples, with the exception of those which are short-circuited, demonstrate a similar compartment, the resistance varying however by 50% according to the sample, this being explained by the weak reproducibility of the deposits at the brush. Nevertheless, the relative variation of resistance with oxygen pressure is not identical and in particular does not depend on the composition of the sample within the tested range.

D. Influence of temperature on the resistance.

Figure 5:
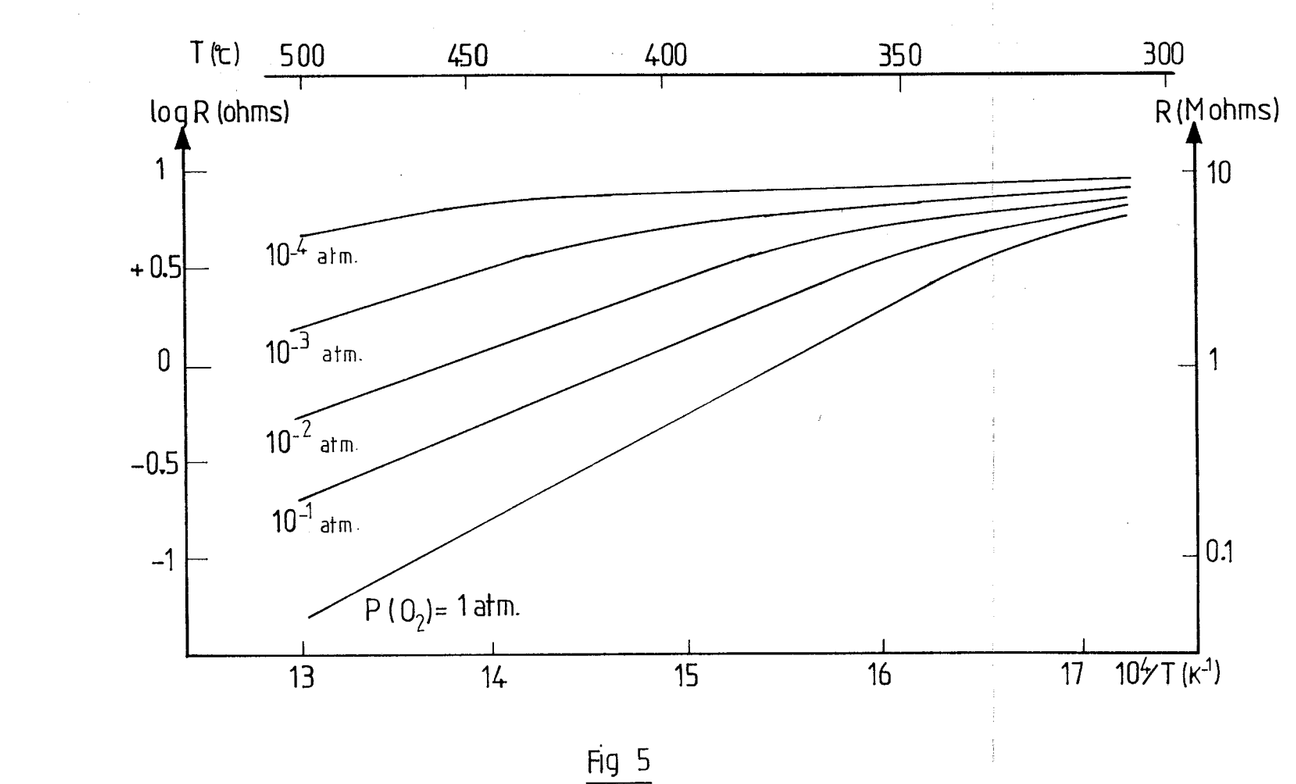
FIG. 5 is a diagram illustrating the influence of temperature on the present invention at different oxygen pressures.

The curves of FIG. 5 show the influence of temperature on the resistance for the tested pressures of oxygen. The electrochemical reactions as well as the numerous diffusion phenomena are from the processes activated thermally, where the kinetics are more often proportional to the expression $(-E/kT)$. It is because of this that the logarithm of the resistance as a function of the inverse of the temperature is represented, and effectively, we obtain practically straight lines for the temperatures superior to 350 degrees and with high oxygen pressures.

At the lowest temperatures, the curves approach each other, which signifies that at that time the phenomenon limiting the conduction no longer depends on the oxygen pressure. This shows then a lower utilization limit around 300 degrees, with the materials and geometry studied.

E. Influence of measured electrical tension.

Figure 6:
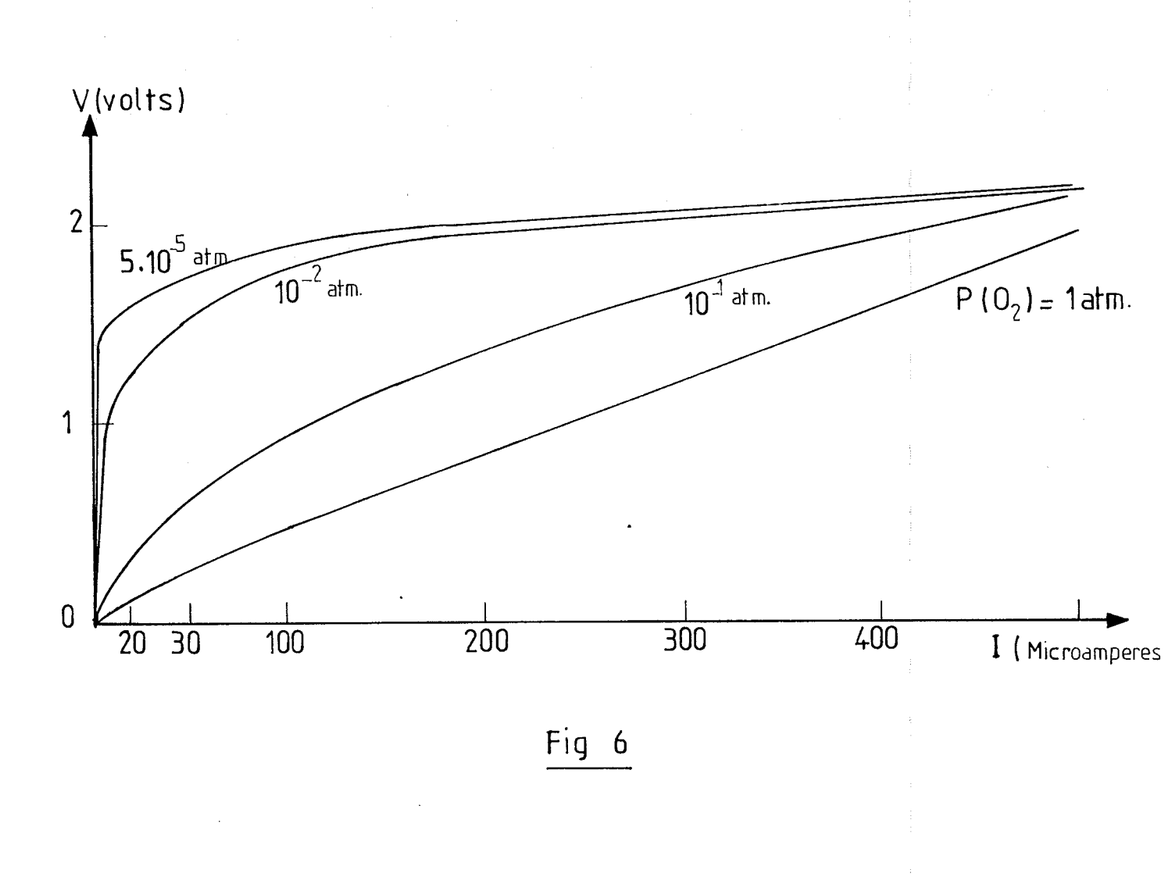
FIG. 6 is a diagram of curves of the influence of different voltage on samples according to the invention.

The curves in FIG. 6 show that the comportment of the material is not linear. Above 1.5 to 2 Volts at 400 degrees an electrolysis of the zirconium begins. The curves show that the measuring voltage, with the tested composition and geometry, is most favorable in the range from 0.5 to 1.5 volts.

F. Analysis of the complex admittance of the samples.

Figure 7:
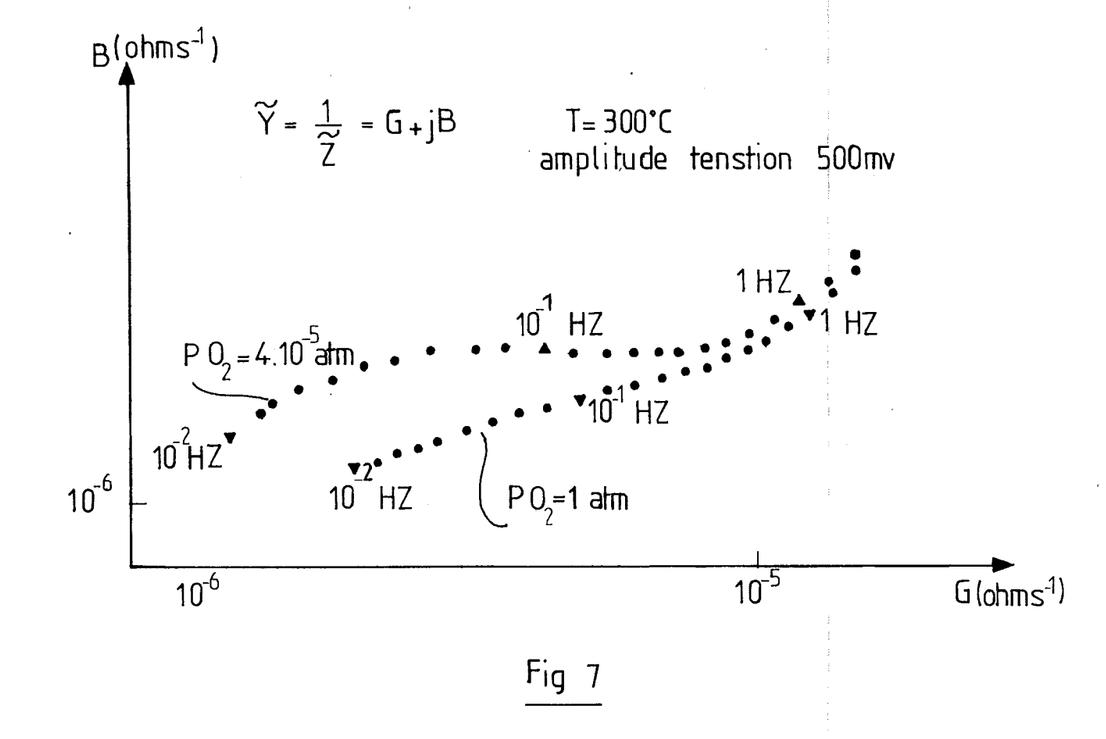
FIG. 7 is a diagram of analysis of admittance of samples according to the present invention.

It is possible, by representing the imaginary part of the admittance B as a function of its real part, to show that the influence of the oxygen pressure exerted on the phenomenon where the response time at 300 degrees is of the order of a second (See FIG. 7).

Figure 8:
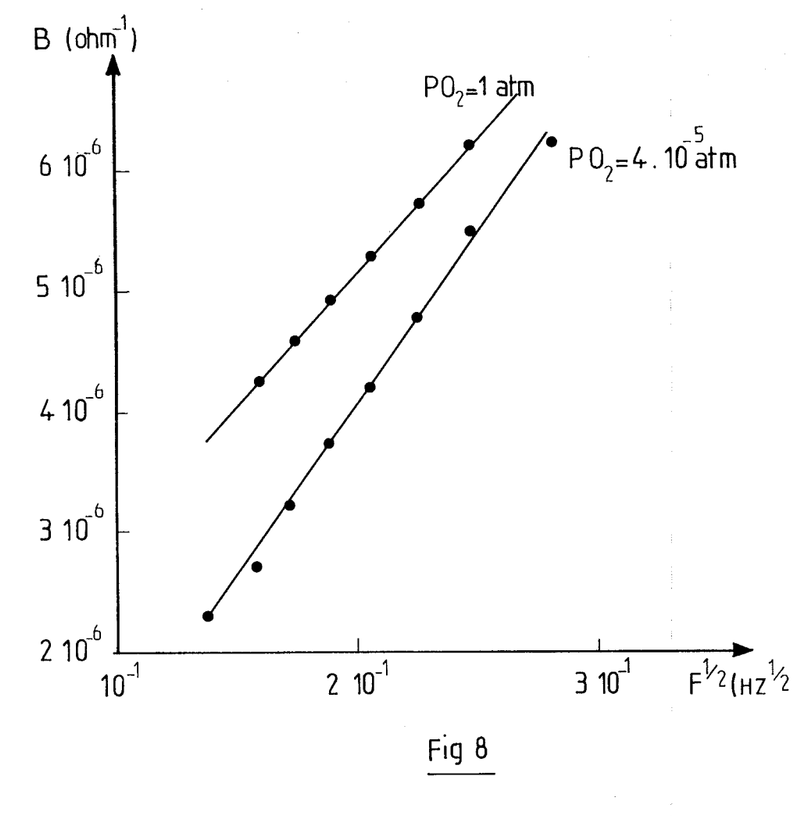
FIG. 8 is a diagram illustrating an admittance characteristic of a sample, according to the invention, usable for fabrication of oxygen detectors.

If at a constant temperature and constant oxygen pressure, one represents the imaginary part of the admittance as a function of the square root of the frequency, one can verify a factor called "de Warburg" by the electrochemists, characteristic of a limitation by the phenomenon of diffusion of a chemical species, without being capable of specifying actually which it is. FIG. 8 shows an example for a sample containing a 40% platinum mass, at 300 degrees between $4 \cdot 10^{-5}$ and 1 atmosphere of oxygen.

This new composite material then provides a considerable relative variation of the equivalent of the conductivity of direct current with the pressure of oxygen. This permits the fabrication of oxygen detectors extremely simple and susceptible of operating at moderate temperatures. In addition, such detectors will be adaptable for applications on small and medium capacity burners and for the control of combustion of internal combustion motors. The measuring voltages, of a few volts, are well adapted to the safety, insensibility to exterior noise perturbations and simplification of the signal exploitation device imperatives.

All of the methods of realizing electrical resistances are applicable to the fabrication of devices according to the invention provided that the distance between the metallic electrodes be sufficient to contain a large number of elementary cells: pastilles, serigraph and analogic.

The electrochemical cells are realized by firing or fritting a mixture of microscopic metal particles and a solid solution of oxides (or of the component oxides) according to the usual methods for powder metallurgy, or by depositing by brush or serigraphy a thick layer of a mixture of constituents, followed by a firing or fritting.

In these conditions, the distribution of the microcells is aleatory at the microscopic level, but the macroscopic comportment is reproducible and reflects the influence of the pressure of the oxygen on the kinetics of the exchanges to the triple contacts, gas-metal-oxide, or to the double contacts, metal-oxide.

As oxide ionic conductors of oxygen ions, one can cite the fluorine lacunal structure oxides such as zircon, thorite, hafnium or cerium or their solid solutions, to which have been incorporated one or several oxides conferring to them this conductivity: rare earth oxide, limestone, magnesia, oxide of bismuth . . . The whole can be porous or not.

The advantages of the devices according to the invention are essentially of two orders:

In the first place, those which are associated by their operation at a low temperature, of the order of 300° to 600° C.: easy to control the temperature, minimum consumption of energy, thence the possibility of mobile use, practically instantaneous start-up, possibility of gas dosage outside of an established equilibrium, low cost annex material and technology.

In the second place, those which are associated to the easy miniaturization of these devices, here one can note the minimum energy consumption, but as well: low thermal inertia, whence the convenience of intermittent usages, high resistance to thermal shocks, reduced response time, low percentage of "precious" material.

Figure 9:
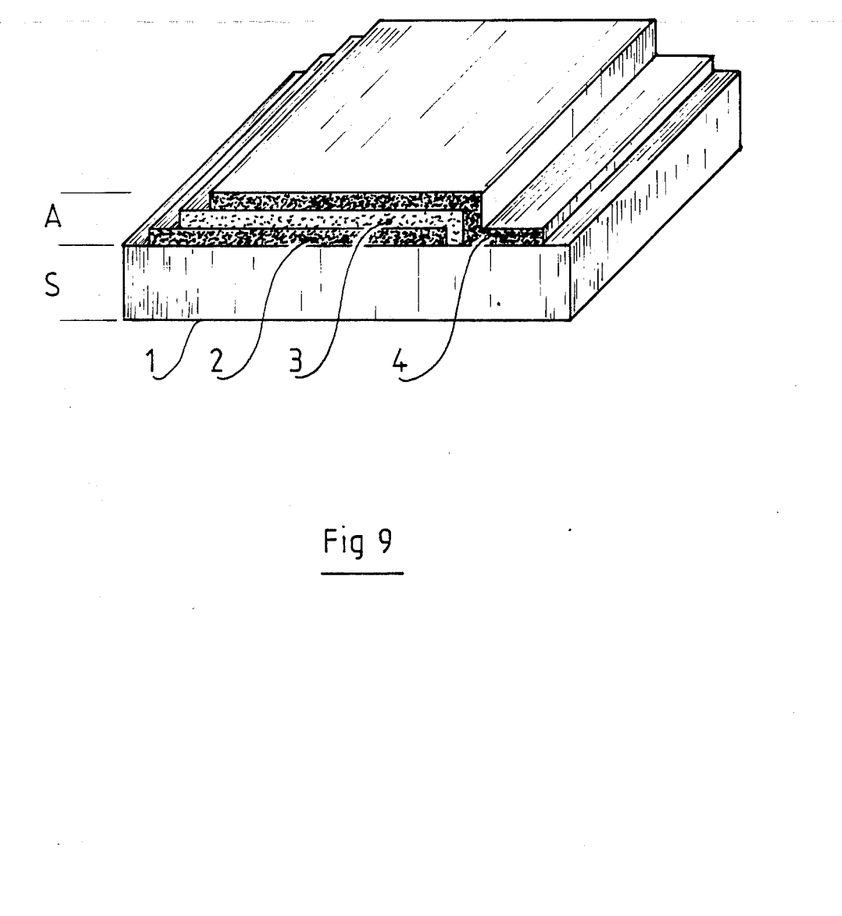
FIG. 9 is a schematic diagram of the structure of a device constructed according to the invention.

Represented also as an example of a practical realization on FIG. 9 is how a device is presented according to the invention. On this drawing, the references have the following signification:

A: zone responsive to oxygen pressure
S: support zone, having only a mechanical role
1 substratum, of alumina (can be zircon)
2 lower metallic or percolated cerium metal (high percentage of metal) electrode
3 cerium metal/electrolyte (non-percolated metal)
4 upper metallic or percolated cerium metal (high percentage of metal) electrode
(3 and 4 must be porous).

Moreover, one can add to these advantages: simple structure, absence of joints, assemblies and adjustments, easy exploitation of the signal, reliability, fabrication in large series and at a moderate cost possible because of proven simple methods.

Figure 10:
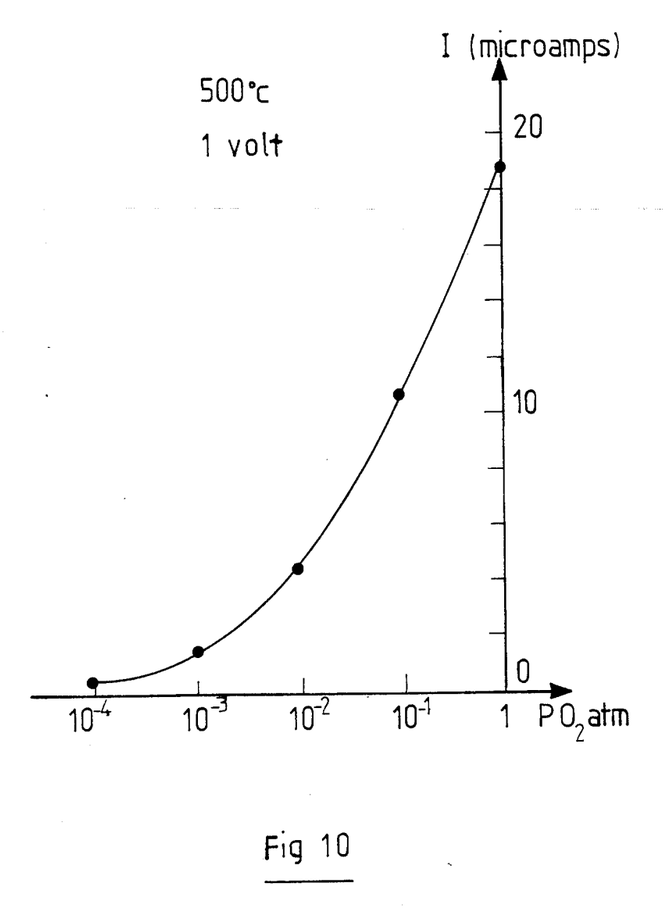
FIGS. 10 and 11 are diagrams of curves of direct current electrical measurements made on layers of a sandwich structure according to the invention.
Figure 11:
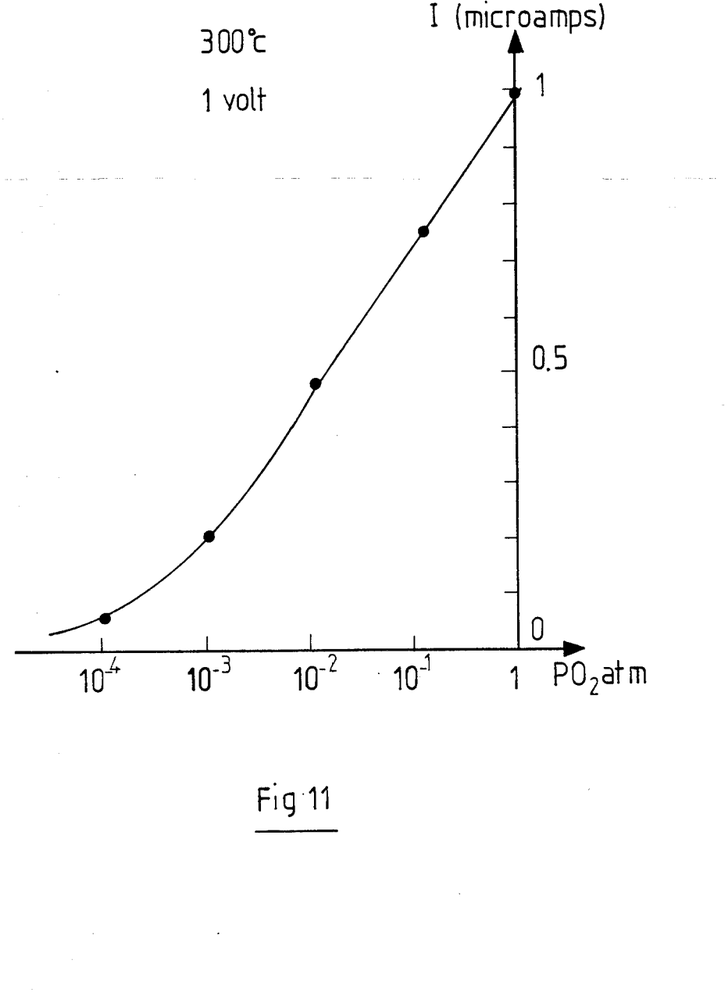

Finally, FIGS. 10 and 11 illustrate the results obtained using gauges according to the invention entirely serigraphed on a substratum of alumina, according to the following process:

Basic inks:
Platinum ink fabricated by EMCAR (England) and commercialized by Comatel. Lot 2GO 90 884, containing 70% of platinum by weight.

Cerium metal ink fabricated at the laboratory of the deponent by mixing intimately zircon (stabilized by a 12% mass of yttrium, of Zircar origin), and the platinum ink above in the appropriate proportions to obtain after firing and elimination of the organic carrier of a mass of 50% platinum and 50% zircon.

The successive deposits are the following:
two layers of platinum ink followed by drying (1 hour at 200 degrees),
firing at 1150 degrees, 30 minutes,
four layers of cerium metal, each followed by drying (1 hour at 200 degrees) and firing (1450 degrees, 15 minutes),
firing of the whole at 1450 degrees, 5 hours,
two layers of platinum ink followed by drying (1 hour at 200 degrees) and firing at 950 degrees, 30 minutes.

Thus one obtains a "sandwich" structure constituted by a non-percolated layer of cerium metal, of a thickness of about 20 microns (deposit of 20 mg of cerium metal); between two continuous electrodes of platinum of a thickness of about 4 microns (deposit of about 8 mg).

The wires are connected to the end electrodes of the assembly and introduced into the measuring device already described (a controlled atmosphere of nitrogen-+oxygen mixture furnace).

The electrical measures shown on the curves of FIGS. 10 and 11 are made with a direct current of 1 volt, and the current is measured, the upper electrode being positive.

It was noted as well that an increase of the surface permitted the dimunition of the resistance by a factor of at least 50, which authorizes the exploitation as low as 300° C.

We claim:

1. A composite material sensitive to weak variation of oxygen pressure at low temperature, comprising (a) microscopic particles of an ionic conductor of oxygen ions, wherein the ionic conductor is a solid solution of lower valence metal oxides in tetravalent metal oxides, in which the metal of the lower valence metal oxides has a valence of less than four, and (b) discrete microscopic particles of an electronic conductor.

2. The composite material according to claim 1 in which the electronic conductor is a metal chosen from platinum, gold, palladium, silver or an alloy thereof.

3. The composite material according to claim 1 in which the microscopic particles have been fired or fritted.

4. The composite material according to claim 2 in which the microscopic particles have been fired or fritted.

5. The composite material according to any one of claims 1 or 2 in which the microscopic particles have been fired and firing is carried out using a shaping carrier which is nonconductive and disappears during the firing.

6. The composite material according to any one of claims 1, 2, 3 or 4 in which the composite material is deposited on a support.

7. The composite material according to claim 6 in which the composite material is deposited on a support of alumina or zircon.

8. An oxygen sensor comprising the composite material according to any one of claims 1, 2, 3 or 4.

9. An oxygen sensor comprising the composite material according to claim 5.

10. An oxygen sensor comprising the composite material according to claim 6.

* * * * *